(12) United States Patent
Damak et al.

(10) Patent No.: US 12,167,742 B2
(45) Date of Patent: Dec. 17, 2024

(54) NUTRITIONAL COMPOSITION COMPRISING 6'SL AND LNT IN COMBINATION TO IMPROVE THE GASTROINTESTINAL BARRIER FUNCTION

(71) Applicant: SOCIETE DES PRODUITS NESTLE S.A., Vevey (CH)

(72) Inventors: Sami Damak, Lausanne (CH); Francis Foata, La Conversion (CH); Norbert Sprenger, Savigny (CH)

(73) Assignee: Societe des Produits Nestle S.A., Vevey (CH)

( * ) Notice: Subject to any disclaimer, the term of this patent is extended or adjusted under 35 U.S.C. 154(b) by 664 days.

(21) Appl. No.: 17/416,578

(22) PCT Filed: Dec. 6, 2019

(86) PCT No.: PCT/EP2019/083957
§ 371 (c)(1),
(2) Date: Jun. 21, 2021

(87) PCT Pub. No.: WO2020/126542
PCT Pub. Date: Jun. 25, 2020

(65) Prior Publication Data
US 2022/0287349 A1 Sep. 15, 2022

(30) Foreign Application Priority Data
Dec. 21, 2018 (EP) .................................. 18215378

(51) Int. Cl.
*A23L 33/00* (2016.01)
*A23L 33/21* (2016.01)

(52) U.S. Cl.
CPC ............... *A23L 33/40* (2016.08); *A23L 33/21* (2016.08)

(58) Field of Classification Search
CPC ....................................................... A23L 33/40
See application file for complete search history.

(56) References Cited

U.S. PATENT DOCUMENTS

2012/0171166 A1 7/2012 Chow et al.
2016/0296540 A1* 10/2016 Sangild ................ A61K 35/741
2017/0295838 A1* 10/2017 Destaillats .............. A23L 33/30
(Continued)

FOREIGN PATENT DOCUMENTS

| WO | 2013032674 A1 | 3/2013 |
| WO | 2015071401 | 5/2015 |
| WO | 2015071402 | 5/2015 |

(Continued)

OTHER PUBLICATIONS

Kuznetsova, "Parentheses in the Text of a Legal Document as a Linguo-Cognitive Phenomenon", Russian Philology, Issue No. 03, 2015, pp. 37-43.
(Continued)

*Primary Examiner* — Jenna A Watts
(74) *Attorney, Agent, or Firm* — K&L Gates LLP (57) ABSTRACT

The present invention relates to nutritional compositions comprising 6'-sialyllactose (6'SL) and lacto-N-tetraose (LNT) for use in improving the gastrointestinal barrier. In particular, the present invention relates to improving gut barrier function in an infant, a young child or children aged above 3 years to 8 years.

12 Claims, 6 Drawing Sheets

(56) References Cited

U.S. PATENT DOCUMENTS

2020/0260771 A1 * 8/2020 McConnell .......... A23L 33/135

FOREIGN PATENT DOCUMENTS

| WO | 2015071403 | 5/2015 | | |
|----|----|----|----|----|
| WO | 2016066174 | 5/2016 | | |
| WO | 2016091265 | 6/2016 | | |
| WO | WO-2017103019 A1 * | 6/2017 | .......... | A23L 33/135 |
| WO | 2019121929 | 6/2019 | | |

OTHER PUBLICATIONS

Office Action Received for Application No. RU2021119918, mailed on Mar. 14, 2023, 7 Pages of Official Copy.

Taylor et al. "Intestinal Permeability in Preterm Infants by Feeding Type: Mother's Milk Versus Formula" Breastfeeding Medicine, 2009, vol. 4, No. 1, pp. 11-15.

Ma et al. "Lactational changes in the human milk oligosaccharide concentration in Chinese and Malaysian mothers' milk" International Dairy Journal, 2018, vol. 87, pp. 1-10.

"Enteral and Parenteral Nutrition", Nanjing Military Region Nanjing General Hospital, Oct. 31, 1992, 4 Pages.

Chinese Office Action for Appl No. 201980077766.0 dated Nov. 20, 2023.

Russian Office Action for Appl No. 2021119918/10 dated Nov. 1, 2023.

\* cited by examiner

NUTRITIONAL COMPOSITION COMPRISING 6'SL AND LNT IN COMBINATION TO IMPROVE THE GASTROINTESTINAL BARRIER FUNCTION

CROSS REFERENCE TO RELATED APPLICATIONS

The present application is a National Stage of International Application No. PCT/EP2019/083957, filed on Dec. 6, 2019, which claims priority to European Patent Application No. 18215378.3, filed on Dec. 21, 2018, the entire contents of which are being incorporated herein by reference.

TECHNICAL FIELD OF THE INVENTION

The present invention relates to nutritional compositions comprising 6'-sialyllactose (6'SL) and lacto-N-tetraose (LNT) for use in improving the gastrointestinal barrier. In particular, the present invention relates to improving gut barrier function in an infant, a young child or children aged above 3 years to 8 years.

BACKGROUND OF THE INVENTION

Mother's milk is recommended for all infants. However, in some cases breast feeding is inadequate or unsuccessful for medical reasons or the mother chooses not to breast feed. Infant formulae have been developed for these situations. Fortifiers have also been developed to enrich mother's milk or infant formula with specific ingredients. In such cases, it would be even more preferred to provide means to improve gut barrier function in infants and young children through nutritional intervention.

During the postnatal development, the newborn intestine experiences a process of maturation that ends by the establishment of a structurally intact and functional barrier to macromolecules and pathogenic bacteria. This phenomenon is called gut closure and appears to be affected by the diet. Hence, different studies with infants (JPGN, 1995, 21: 383-6) and animal models (Pediatr Res, 1990, 28: 31-7) show that the maturation of the barrier is faster in breast-fed than in formula-fed newborns. This could explain the higher prevalence of allergy and infection in infants fed formula than in those fed with mother milk.

Some specific populations of infants and young children are particularly in need of compositions able to improve gut barrier function. Such infants and young children are for example preterm infants, low birth weight infant, and/or growth-retarded infants or young children. Indeed the gut barrier is more permeable and more susceptible to injury and its structure and function are less mature in such infants than in a healthy term infant. This in turn may lead to other problems such as infection or allergy. For such infants it is particularly advantageous to complement pharmacological management with nutritional compositions capable of improving gut barrier function.

The effect of nutritional ingredients, such as human milk oligosaccharides to improve gut barrier function has previously been investigated.

WO2013/032674 describes that human milk oligosaccharides may be favourable to the gut barrier function. 6'SL and LNT are mentioned among long lists of examples of suitable HMOs.

A favourable effect of LNT, among other HMOs, has also been described in WO2017/46711 (treat impaired mucosal barrier), WO2017/71716 (treat impaired mucosal barrier), WO2016/91265 (decrease gut permeability) and WO2016/66174 (maintain mucosal integrity). In WO2015/091789 the beneficial effect of N-acetylated oligosaccharides, such as for example LNT, in combination with sialylated oligosaccharides and galactooligosaccharides to decrease gut permeability has been described. Also in WO2015/071403 LNT is described as promoting gut functional maturation.

Increased enterocyte migration is an important mechanism after mucosal injury for rapid restoration of epithelial continuity over the denuded villus surface area. Tsukahara et al. has found that activation of GPR35 promotes mucosal repair in the colon (Pharmacological Research 123 (2017) 27-39). Such mechanism is associated with improved gastrointestinal barrier function, structure, protection, and maturation, and in particular with improved gastrointestinal barrier function, structure and protection.

It would be useful to further optimize the effect of nutritional compositions on gut barrier function in all infants and children.

There is clearly a need for developing suitable methods to improve gut barrier function in infants and young children.

There is also a need to deliver such health benefits in a manner that is particularly suitable for the young subjects (infants and young children), that does not involve a classical pharmaceutical intervention, as these infants or young children are particularly fragile.

There is a need to deliver such health benefits in these infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

There is thus clearly a need to develop alternative methods than the classical pharmaceutical intervention such as the use of pharmaceuticals, at least because of the associated risk of side effects.

SUMMARY OF THE INVENTION

As outlined above, it has previously been found that the activation of GPR35 promoted mucosal repair in the colon (Tsukahara et al. Pharmacological Research 123 (2017) 27-39). The present invention is based on the realization of a synergistic effect of the combination of 6'SL and LNT on activation of the GPR35 receptor, wherein the effect of the combination is larger than the sum of 6'SL and LNT alone (see example 2). Therefore, it has been found that a combination of 6'SL and LNT synergistically improves the gut barrier.

Thus, an object of the present invention relates to nutritional compositions for improving the gut barrier, such as improving barrier repair, improving barrier maturation, improving barrier structure, and/or improving barrier protection.

Thus, one aspect of the invention relates to a nutritional composition comprising 6'-sialyllactose (6'SL) and lacto-N-tetraose (LNT) for use in improving the gastrointestinal barrier in an infant (child under the age of 12 month) or a young child (between 1 year and less than 3 years); or a nutritional composition in the form of a growing-up milk comprising 6'-sialyllactose (6'SL) and lacto-N-tetraose (LNT) for use in improving the gastrointestinal barrier in children (aged from 3 years to less than 8 years).

In a preferred embodiment of the invention, said improvement to the gastrointestinal barrier is improved barrier repair, such as mucosal repair in the colon, which is linked to activation of GPR35. In turn, improving barrier repair is important for restoring barrier structure and function. Improved repair is thus associated with improved barrier structure and function, as well as barrier protection.

Maturation, structure, function, and repair of the gastrointestinal barrier are all interrelated. Proper gastrointestinal maturation leads to proper gastrointestinal structure and function, which in turn are maintained by proper barrier protection and restored by proper barrier repair. Thus, any of these aspects considered together or individually contribute to sustained reduction of disease susceptibility.

The present invention will now be described in more detail in the following.

DETAILED DESCRIPTION OF THE INVENTION

Definitions

Prior to discussing the present invention in further details, the following terms and conventions will first be defined:

The term "infant" means a child under the age of 12 months (<12 month). The expression "young child" means a child aged between one and less than three years (1 year to <3 years), also called toddler. The expression "child" means a child between three and less than eight years of age ((≥3 year to <8 years). An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 37 weeks of gestation.

An "infant having a low birth weight" means a new born having a body weight below 2500 g (5.5 pounds) either because of preterm birth or restricted fetal growth. It therefore encompasses:

infant or young child who has/had a body weight from 1500 to 2500 g at birth (usually called "low birth weight" or LBW)

infant or young child who has/had a body weight from 1000 to 1500 g at birth (called "very low birth weight" or VLBW)

infant or young child who has/had a body weight under 1000 g at birth (called "extremely low birth weight" or ELBW).

An "infant born small for gestational age (SGA)" means a baby with birth weights below the $10^{th}$ percentile for babies of the same gestational age.

The expression "nutritional composition" means a composition which nourishes a subject. This nutritional composition is usually to be taken orally, and it usually includes a lipid or fat source and a protein source.

In a particular embodiment, the composition of the present invention is a hypoallergenic nutritional composition. The expression "hypoallergenic nutritional composition" means a nutritional composition which is unlikely to cause allergic reactions.

In a particular embodiment, the composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" (or GUM) refers to a milk-based drink generally with added vitamins and minerals, that is intended for young children or children.

The term "fortifier" refers to liquid or solid nutritional compositions suitable for mixing with breast milk or infant formula.

The expression "weaning period" means the period during which the mother's milk is substituted by other food in the diet of an infant or young child.

The expressions "days/weeks/months/years of life" and "days/weeks/months/years of birth" can be used interchangeably.

The expression "improved gastrointestinal barrier", may encompass one or several of the following:

Improved barrier repair, such as (but not limited to) recovery of the integrity of the gastrointestinal barrier, such as repair of a disrupted barrier, reduction of permeability upon inflammatory challenge of the gastrointestinal mucosa, and mucosal repair.

Improved barrier maturation, such as (but not limited to) maturation and/or development of the barrier of an infant, preferably of a preterm infant.

Improved barrier structure, such as (but not limited to) strengthening of the gastrointestinal barrier, integrity of the gastrointestinal barrier, tight junction structure, and intestinal epithelial lining integrity.

Improved barrier function, such as improvement of gastrointestinal barrier resistance, reduction of gastrointestinal barrier permeability, such as reduction of pathogens to migrate out of the gut through the intestinal barrier, such as reduction of commensal bacteria to migrate out of the gut through the intestinal barrier, reduction of allergens to migrate out of the gut through the intestinal barrier, reduction of toxic compounds to migrate out of the gut through the intestinal barrier and reduction of disease susceptibility.

Improved barrier protection, such as (but not limited to) prevention of barrier dysfunction, prevention of barrier leakiness, protection of tight junction structure, protection of the intestinal epithelial lining integrity.

The "mother's milk" should be understood as the breast milk or the colostrum of the mother.

An "oligosaccharide" is a saccharide polymer containing a small number (typically three to ten) of simple sugars (monosaccharides).

The term "HMO" or "HMOs" or "HMO's" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2'FL (2'-fucosyllactose), 3'FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyl-lacto-N-neohexaose, difucosyllacto-N-hexaose I, difucosyllacto-N-neohexaose II and any combination thereof. Without wishing to be bound by theory it is believed that the fucosyl-epitope of the fucosylated oligosaccharides may act as decoy at the mucosal surface. By a competition effect, it may prevent and/or limit the action of the pathogens responsible of infections (of viral or bacterial origin) or of their secreted components (e.g. toxins), especially by avoiding their binding to natural ligands, and without to be bound by theory, this is believed to therefore reduce the risk of infections/inflammations, and particularly the risk of LRT/ear infections and/or inflammations. In addition, the fucosylated oligosaccharides are thought to boost growth and metabolic activity of specific commensal microbes reducing inflammatory response and creating an environment unfavourable for pathogens thus leading to colonization resistance.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected. Without wishing to be bound by theory the 2'-fucosyl-epitope of these fucosylated oligosaccharides is believed to be particularly specific to pathogens (or their secreted components) involved in the LRT and/or ear infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) and any combinations thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

The expression "at least one fucosylated oligosaccharide" and "at least one N-acetylated oligosaccharide" means "at least one type of fucosylated oligosaccharide" and "at least one type of N-acetylated oligosaccharide".

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3'SL (3' sialyllactose) and 6'SL (6' sialyllactose).

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or a follow-on/follow-up formula or a growing-up milk or an infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

Nutritional Composition

The present invention is based on the identification of a synergistic effect of the combination of 6'SL and LNT on activation of the GPR35 receptor. Such synergistic effect of 6'SL and LNT on activation of the GPR35 receptor is relevant for improvement of the gut barrier.

Thus, an aspect of the invention relates to a nutritional composition comprising 6'-sialyllactose (6'SL) and lacto-N-tetraose (LNT) for use in improving the gastrointestinal barrier in an infant (child under the age of 12 month) or a young child (between 1 year and less than 3 years); or a nutritional composition in the form of a growing-up milk comprising 6'-sialyllactose (6'SL) and lacto-N-tetraose (LNT) for use in improving the gastrointestinal barrier in a child (aged from 3 years to less than 8 years). As shown in example 2, a synergistic effect of the combination of 6'SL and LNT on activation of the GPR35 receptor has been identified.

As also outlined above, improved barrier repair has been linked to activation of GPR35 (Tsukahara et al. Pharmacological Research 123 (2017) 27-39). Thus, activation of the GPR35 receptor improves barrier repair, which is considered important for barrier maturation. Improved repair/maturation results in improved barrier structure, which leads to improved barrier protection. Thus, in an embodiment, said improvement to the gastrointestinal barrier is improved barrier repair, improved barrier function, improved barrier structure, and/or improved barrier protection.

In another embodiment, said improvement to the gastrointestinal barrier is improved barrier repair, improved barrier structure, and/or improved barrier function.

In a preferred embodiment, said improvement to the gastrointestinal barrier is improved barrier repair.

In another embodiment, said use is for improving the recovery of the integrity of the gastrointestinal barrier, such as repair of a disrupted barrier, reduction of permeability upon inflammatory challenge of the gastrointestinal mucosa, and mucosal repair.

In yet another embodiment, said use is for improving the strength of the gastrointestinal barrier, improving the gastrointestinal barrier resistance, reducing the disease susceptibility, reducing the severity of symptoms upon inflammatory challenge of the gastrointestinal mucosa and/or reducing the gastrointestinal barrier permeability.

In yet another embodiment, said reduction in the gastrointestinal barrier permeability is reduction in pathogens, allergens and/or toxic compounds migrating from the gut into the body through the intestinal barrier.

The above outlined effects/benefits are preferably obtained in the small intestine.

In an embodiment, the nutritional composition is formulated for administration to an infant. In a related embodiment, said infant is selected from the group consisting of premature, small for gestational age and low birth weight babies, preferably the infant is premature. The nutritional compositions according to the invention are considered particularly useful for these types of infants, since the described benefits are more important for these infants than for "normal" infants, because the barrier is less mature and more permeable than in the healthy term infant.

In an embodiment, said nutritional composition is an infant formula, a starter infant formula, a follow-on or follow-up infant formula, a growing-up milk, a baby food, an infant cereal composition, a fortifier or a supplement and is for administration to an infant or a young child.

In a particularly advantageous embodiment of the present invention, 6'SL and LNT are present in the nutritional composition or the growing-up milk in some particular amounts.

In yet an embodiment, 6'SL and LNT are present in a weight ratio 6'SL:LNT of from 3:1 to 1:3, such as 2:1 to 1:2 or 2:1 to 1:1. In a particularly advantageous embodiment, this ratio is 2:1 or around 2.1 preferably this ratio is 1:1 or around 1:1.

In another embodiment, 6'SL is present in an amount of 0.005 to 5 g/L or 0.004 to 3.8 g/100 g of composition on a dry weight basis.

In a further embodiment, LNT is present in an amount of 0.005-3 g/L or 0.004-2.3 g/100 g of composition on a dry weight basis.

In yet a further embodiment, the nutritional composition comprises
 6'SL in an amount of 0.24 or 0.05 g/L of the composition and/or in an amount of 0.18 or 0.04 g/100 g of composition on a dry weight basis; and/or
 LNT in an amount of 0.5 g/L or 0.1 g/L of the composition and/or in an amount of 0.38 g/100 g of composition or 0.08 g/100 g of composition on a dry weight basis.

In a preferred embodiment of the invention, LNT is present in the nutritional composition or the growing-up milk in an amount of 0.005-3 g/L of the composition. In some embodiments, LNT may be in an amount of 0.01-1.5 g/L of the composition, such as 0.04-1.2 g/L or 0.05-1 g/L or 0.09-0.8 g/L of the composition. In a particular embodiment, LNT is in an amount of 0.5 g/L of the composition. In another particular embodiment, LNT is in an amount of 0.1 g/L of the composition.

LNT can be present in the nutritional composition or the growing-up milk in an amount of 0.004-2.3 g/100 g of composition on a dry weight basis, LNT may be present in an amount of 0.008-1.2 g/100 g of composition, such as 0.03-0.9 g/100 g or 0.04-0.8 g/100 g or 0.07-0.6 g/100 g of the composition. In a particular embodiment, LNT is present in an amount of 0.38 g/100 g of the composition. In another particular embodiment, LNT is present in an amount of 0.08 g/100 g of the composition.

LNT may be synthesised chemically by enzymatic transfer of saccharide units from donor moieties to acceptor moieties using glycosyltransferases as described for example in U.S. Pat. No. 5,288,637 and WO 96/10086.

In another preferred embodiment of the invention the nutritional composition or the growing-up milk may comprise from 0.005-5 g/L of 6'SL, or from 0.008-2.5 g/L, or from 0.01-1 g/L, or from 0.03-0.7 g/L, for example 0.04 or 0.5 g/L.

The nutritional composition or the growing-up milk according to the invention can contain 0.004-3.8 g of 6'SL per 100 g of composition on a dry weight basis, e.g. 0.006-1.9 g or 0.008-0.8 g or 0.023-0.5 g or 0.031-0.4 of 6'SL per 100 g of composition on a dry weight basis, for example 0.18 g or 0.04 g per 100 g of composition on a dry weight basis.

6'SL may be isolated by chromatographic or filtration technology from a natural source such as animal milks.

Alternatively, it may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. 6'SL formation can be initiated by acceptor substrates starting from any degree of polymerisation (DP), from DP=1 onwards. Alternatively, 6'SL may be produced by chemical synthesis from lactose and free N'-acetylneuraminic acid (sialic acid).

In a particular aspect of the invention, the nutritional composition or the growing-up milk comprises 6'SL and LNT wherein:
  6'SL is in an amount of 0.005-5 g/L of the composition and/or in an amount of 0.004-3.8 g/100 g of composition on a dry weight basis; and/or
  LNT is in an amount of 0.005-3 g/L of the composition and/or in an amount of 0.004-2.3 g/100 g of composition on a dry weight basis.

In a particular aspect of the invention, the nutritional composition or the growing-up milk comprises 6'SL and LNT wherein:
  6'SL is in an amount of 0.008-2.5 g/L of the composition and/or in an amount of 0.006-1.9 g/100 g of composition on a dry weight basis; and/or
  LNT is in an amount of 0.01-1.5 g/L of the composition and/or in an amount of 0.008-1.2 g/100 g of composition on a dry weight basis.

In another particular embodiment the nutritional composition or the growing-up milk of the present invention comprises 6'SL and LNT wherein:
  6'SL is in an amount of 0.01-1 g/L of the composition and/or in an amount of 0.008-0.8 g/100 g of composition on a dry weight basis; and/or
  LNT is in an amount of 0.04-1.2 g/L of the composition and/or in an amount of 0.03-0.9 g/100 g of composition on a dry weight basis.

In another particular embodiment the nutritional composition or the growing-up milk of the present invention comprises 6'SL and LNT wherein:
  6'SL is in an amount of 0.03-0.7 g/L of the composition and/or in a total amount of 0.023-0.5 g/100 g of composition on a dry weight basis; and/or
  LNT is in an amount of 0.05-1 g/L of the composition and/or in an amount of 0.04-0.8 g/100 g of composition on a dry weight basis.

In another particular embodiment the nutritional composition or the growing-up milk of the present invention comprises 6'SL and LNT wherein:
  6'SL is in an amount of 0.04-0.5 g/L of the composition and/or in an amount of 0.031-0.4 g/100 g of composition on a dry weight basis; and/or
  LNT is in an amount of 0.09-0.8 g/L of the composition and/or in an amount of 0.07-0.6 g/100 g of composition on a dry weight basis.

In a specific embodiment the nutritional composition or the growing-up milk according to the invention comprises 6'SL and LNT wherein:
  6'SL is in an amount of 0.24 or 0.05 g/L of the composition and/or in an amount of 0.18 or 0.04 g/100 g of composition on a dry weight basis; and/or
  LNT is in an amount of 0.5 g/L or 0.1 g/L of the composition and/or in an amount of 0.38 g/100 g of composition or 0.08 g/100 g of composition on a dry weight basis.

In a particular embodiment, 6'SL is provided in the nutritional composition or growing-up milk of the present invention in such an amount that normal consumption of the nutritional composition or growing-up milk would provide to the infant or young child, respectively the child, consuming it a total daily dose of 0.003 to 6.5 g, preferably 0.005-3.3 g or 0.006-1.3 g or 0.02-0.9 g, for example 0.024-0.7 g per day.

In a particular embodiment, the LNT is provided in the nutritional composition or growing-up milk of the present invention in such an amount that normal consumption of the nutritional composition or growing-up milk would provide to the infant or young child, respectively the child, consuming it a total daily dose of 0.003-3.9 g, preferably 0.006-2 g or 0.02-1.6 g or 0.03-1.3 g, for example 0.05-1 g per day.

In particular embodiments of the present invention, the nutritional composition, respectively the growing-up milk, of the present invention can comprise additional human milk oligosaccharides and/or precursors thereof. Even when such human milk oligosaccharide are not effective in activating the GPR35 receptors, these may be added to address other health benefits.

Therefore, in a particular embodiment, the nutritional composition or the growing-up milk further comprises at least one fucosylated oligosaccharide. There can be one or several types of fucosylated oligosaccharide(s). The fucosylated oligosaccharide(s) can indeed be selected from the list comprising 2'-fucosyllactose, 3'fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a particular embodiment, the nutritional composition, respectively the growing-up milk, according to the invention comprises 2'-fucosyllactose (or 2FL, or 2'FL, or 2-FL or 2'-FL). In a particular embodiment, there is no other type of fucosylated oligosaccharide than 2'-fucosyllactose, i.e. the nutritional composition or growing-up milk of the invention comprises only 2'-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

In another particular aspect of the invention, the nutritional composition or the growing-up milk can comprise at least one N-acetylated oligosaccharide in addition to LNT. There can be one or several types of N-acetylated oligosaccharide. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments where LNnT is present the nutritional composition or the growing-up milk can comprise both LNT and LNnT in a ratio LNT:LNnT between 5:1 and 1:2, or from 2:1 to 1:1, or from 2:1.2 to 2:1.6.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyllactosamine produced in this way may then be transferred to lactose as the acceptor moiety.

In a particularly advantageous embodiment of the present invention, the nutritional composition or the growing-up milk comprises 2'-fucosyllactose (2FL) and/or lacto-N-neotetraose (LNnT).

In a particular embodiment, the nutritional composition or the growing-up milk according to the invention can comprise other sialylated oligosaccharide(s) in addition to 6'SL, such as 3'-sialyllactose (3-SL).

The sialylated oligosaccharide(s) may be isolated by chromatographic or filtration technology from a natural source such as animal milks. Alternatively, they may be produced by biotechnological means using specific sialyl-transferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In an embodiment, the composition further comprises one or more HMO's selected from the group consisting of LNnT, 2'FL, diFL, and 3'SL.

In yet an embodiment, the composition further comprises one or more HMO's selected from the group consisting of LNnT, 2'FL, diFL, and 3'SL, such as comprising two or more HMO's selected from the group consisting of LNnT, 2'FL, diFL, and 3'SL, such as three or more HMO's selected from the group consisting of LNnT, 2'FL, diFL, and 3'SL, such as further comprising all of LNnT, 2'FL, diFL, and 3'SL. As mentioned in Example 2, a mix of LNT, 6'SL, LNnT, 2'FL, diFL and 3'SL retains the effect of the combination consisting of 6'SL and LNT.

In a specific embodiment, the nutritional composition of the present invention comprises an oligosaccharide mixture that consists of 6'SL, LNT, 2'FL, DiFL, LNnT and 3'SL.

In another specific embodiment the nutritional composition of the present invention comprises an oligosaccharide mixture that consists of 2'FL, LNnT, 3'SL and 6'SL.

In another specific embodiment the nutritional composition of the present invention comprises an oligosaccharide mixture that consists of 2'FL, DiFL, LNT, 3'SL and 6'SL.

It may also be an advantage not to include further HMO's in the composition. Thus, in an embodiment, HMO's or precursors thereof different from 6'SL and LNT are absent from the nutritional composition, or are present in an total amount of less than 0.1% (w/w), preferably such as less than 0.01% (w/w), or more preferably such as less than 0.001%. As shown in example 2, there is a synergistic effect of a combination consisting of 6'SL and LNT on activation of the GPR35 receptor.

The nutritional composition or the growing-up milk according to the present invention may also comprise other types of oligosaccharide(s) (i.e. other than human milk oligosaccharides mentioned above) and/or at least a fiber(s) and/or at least a precursor(s) thereof. The other oligosaccharide and/or fiber and/or precursor thereof may be selected from the list comprising galacto-oligosaccharides (GOS), fructo-oligosaccharides (FOS), inulin, xylooligosaccharides (XOS), polydextrose and any combination thereof. They may be in an amount between 0 and 10% by weight of composition. In a particular embodiment, the nutritional composition or the growing-up milk can also contain at least one BMO (bovine milk oligosaccharide).

Suitable commercial products that can be used to prepare the nutritional compositions or the growing-up milk according to the invention include combinations of FOS with inulin such as the product sold by BENEO under the trademark Orafti, or polydextrose sold by Tate & Lyle under the trademark STA-LITE®.

The nutritional composition or the growing-up milk according to the present invention may optionally also comprise at least one precursor of oligosaccharide. There can be one or several precursor(s) of oligosaccharide. For example the precursor of human milk oligosaccharide is sialic acid, fucose or a mixture thereof. In some particular embodiments the composition comprises sialic acid.

In particular examples the nutritional composition or the growing-up milk comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide. The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

The nutritional composition or the growing-up milk of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly *Bifidobacteria* and/or *Lactobacilli*.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation KI2, *Bifidobacterium lactis* CNCM 1-3446 sold inter alfa by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition or the growing-up milk according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In yet another embodiment, said nutritional composition further comprises at least one probiotic in an amount of from $10^3$ to $10^{12}$ cfu/g of said composition (dry weight).

In one embodiment the probiotics are viable. In another embodiment the probiotics are non-replicating or inactivated. There may be both viable probiotics and inactivated probiotics in some other embodiments. Probiotic components and metabolites can also be added.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on/follow-up formula.

In some particular embodiments, the composition of the invention is an infant formula, a fortifier or a supplement that may be intended for the first 4, 6 or 12 months of age. In a preferred embodiment the nutritional composition of the invention is an infant formula. It is indeed believed that the nutritional intervention of the invention may be most effective when enacted at an early stage of life (for example the first 1, 4, 6, 12 months of age).

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses. In such cases it is particularly useful to define the amount of 6'SL and LNT and optionally other oligosaccharides in terms or daily dose to be administered to the infant or young child, such as described above.

The nutritional composition of the present invention can be in solid (e.g. powder), liquid or gelatinous form.

In a specific embodiment the nutritional composition is a supplement in powder form and provided in a sachet, in the form of tablets, capsules, pastilles or a liquid, such as a liquid to be dispensed as drops in breast milk or in a nutritional composition or directly in the mouth of an infant or a young child.

In another embodiment, the supplement may further contain a carrier, protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. When the supplement is in powder form, it may comprise a carrier. It is however preferred that the supplement is devoid of a carrier. When the supplement is in the form of a syrup, the HMOs are preferably dissolved or suspended in water acidified with citrate.

Further, the supplement may contain vitamins, minerals trace elements and other micronutrients in accordance with the recommendations of Government bodies such as the USRDA.

The nutritional composition of the present invention can be in solid (e.g. powder), liquid or gelatinous form. In a specific embodiment the nutritional composition is a supplement comprising 6'SL and LNT in a ratio of 1:3 to 3:1, wherein the supplement is in powder form and provided in a sachet, preferably a sachet with 1 to 10 g of the mixture of 6'SL and LNT per sachet, or in the form of a syrup, preferably a syrup with a total solid concentration of 5 to 75 g/100 mL (5 to 75% (w/v)). When the supplement is in powder form, it may comprise a carrier. It is however preferred that the supplement is devoid of a carrier. When the supplement is in the form of a syrup, the HMOs are preferably dissolved or suspended in water acidified with citrate.

The nutritional composition or the growing-up milk according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids. The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

The protein component can alternatively be replaced by a mixture or synthetic amino acid, for example for preterm or low birth weight infants.

In a particular embodiment the nutritional composition or the growing-up milk according to the invention is a hypoallergenic composition. In another particular embodiment the composition according to the invention is a hypoallergenic nutritional composition or growing-up milk.

The nutritional composition or the growing-up milk according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition or the growing-up milk according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, structured triglyceride oil, high oleic sunflower oil and high oleic safflower oil, medium-chain-triglyceride oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition or the growing-up milk of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition or the growing-up milk of the invention may contain emulsifiers and stabilisers such as soy, lecithin, citric acid esters of mono- and diglycerides, and the like.

The nutritional composition or the growing-up milk of the invention may also contain other substances which may have a beneficial effect such as lactoferrin, nucleotides, nucleosides, and the like.

The nutritional composition or the growing-up milk of the invention may also contain carotenoid(s). In some particular embodiments of the invention, the nutritional composition of the invention does not comprise any carotenoid.

The nutritional composition or the growing-up milk according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement. The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition of the present invention may also be used in an infant or a young child that was born by C-section or that was vaginally delivered.

In some embodiments the composition according to the invention can be for use before and/or during the weaning period.

The nutritional composition can be administered (or given or fed) at an age and for a period that depends on the needs.

The nutritional composition can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4, 6 or 12 months of birth of said infant. In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on/follow-up formula.

All patent and non-patent references cited in the present application, are hereby incorporated by reference in their entirety.

The invention will now be described in further details in the following non-limiting examples.

EXAMPLES

Example 1

An example of the composition of a nutritional composition (e.g. an infant formula) according to the present invention is given in the below table 1. This composition is given by way of illustration only.

TABLE 1

Composition of the infant formula of Example 1

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K2 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |

TABLE 1-continued

Composition of the infant formula of Example 1

| Nutrients | | per 100 kcal | per litre |
|---|---|---|---|
| Cu (mg) | | 0.06 | 0.4 |
| Zn (mg) | | 0.75 | 5 |
| Oligosaccharides | 6'SL (g) | 0.035 | 0.24 |
| (HMOs) | LNT (g) | 0.07 | 0.45 |

Example 2

Principle of the Assay

Six human milk oligosaccharides (LNnT, LNT, 2'FL, diFL, 6'SL and 3'SL) were screened for their ability to activate the GPR35 receptor in an in vitro assay. The screening was conducted by DiscoverX (Fremont, Ca, USA) using the PathHunter β-Arresin assay. This assay monitors the activation of GPR35 expressed in cultured cells, using Enzyme Fragment Complementation with β-galactosidase (β-Gal) as the functional reporter. The enzyme is split into two inactive complementary portions, EA and PK, expressed as fusion proteins in the cell. EA is fused to β-Arrestin and PK is fused to GPR35. When the GPR35 is activated and β-Arrestin is recruited to the receptor, PK and EA complementation occurs, restoring β-Gal activity, which is measured using chemiluminescent Detection Reagents.

Methods

The GPR35 cell line was expanded from frozen stocks and cultured according to standard procedures. Cells were seeded in a total volume of 20 µL into white walled, 384-well microplates and incubated at 37° C. for the appropriate time prior to testing. All testing was done in duplicate.

HMO samples were shipped to DiscoverX as concentrated stocks in Phosphate Buffered saline. On the test day, a 5× compound working intermediate was prepared in PBS. An amount of 5 µL of 5× sample was added to cells and incubated at room temperature for 3 to 5 hours.

Assay signal was generated through a single addition of 12.5 µL (50% v/v) of PathHunter Detection reagent cocktail, followed by one-hour incubation at room temperature. Microplates were read following signal generation with a PerkinElmer Envision™ instrument for chemiluminescent signal detection.

Zaprinast (which is known to be an activator of GPR35) was used as positive control.

Percentage activity was calculated using the following formula:

$$\% \text{ Activity} = 100\% \times (\text{mean } RLU \text{ of test sample} - \text{mean } RLU \text{ of vehicle control})/(\text{mean MAX control ligand} - \text{mean } RLU \text{ of vehicle control}).$$

Dose-responses were generated by iterative 3× dilutions of the highest concentration tested (10 mM).

Findings

Figure 1:
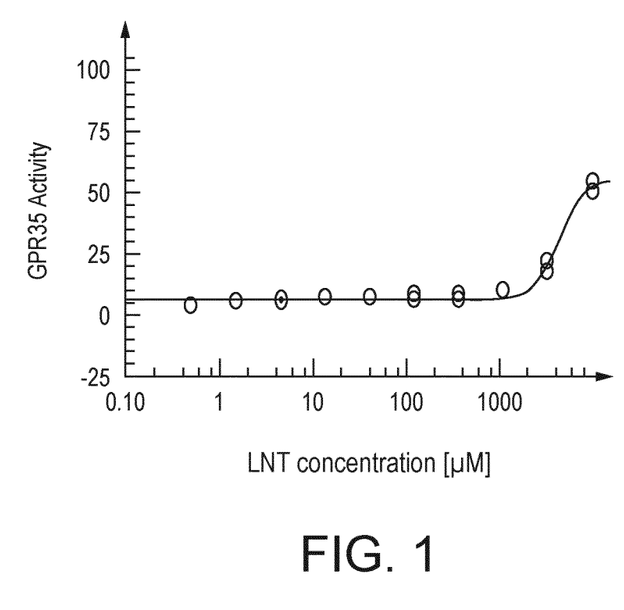
FIG. 1: In vitro response of GPR35 to LNT in the cell based-assay of Example 2. The EC50 value is 4.5 mM.
Figure 2:
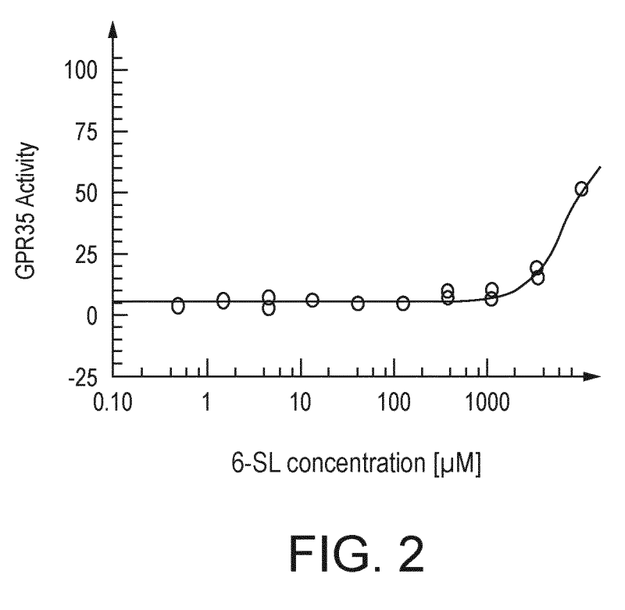
FIG. 2: In vitro response of GPR35 to 6'SL in the cell based-assay of Example 2. The EC50 value is 6.5 mM.

LNT activated GPR35 with an EC50 of 4.5 mM (FIG. 1). 6'SL activated GPR35 with an EC50 of 6.5 mM (FIG. 2). No activation of GPR35 was obtained with 3'SL, 2'FL, diFL and LNnT.

Figure 3:
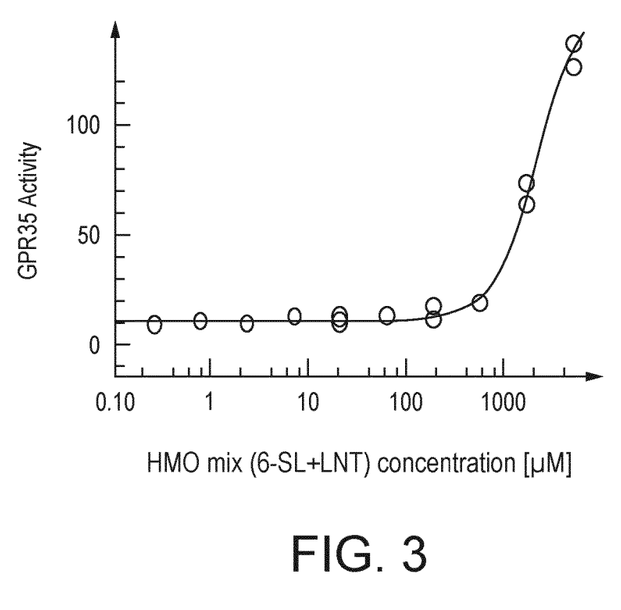
FIG. 3: In vitro response of GPR35 to HMO mix consisting of a mixture of 6'SL and LNT in the cell based-assay of Example 2. The EC50 value is 2.2 mM.

As LNT and 6'SL were found as being activators, these two HMOs were tested in combination. An equimolar mix of 6'SL and LNT activated GPR35 with an EC50 of 2.2 mM (FIG. 3). These results demonstrate a synergy between 6'SL and LNT. A mixture of all six HMOs at an equimolar ratio was also tested, showing similar results as with the combination of LNT and 6'SL. These results demonstrate that the synergistic effect of LNT and 6'SL is maintained even when admixed with other human milk oligosaccharides.

CONCLUSION

In sum, the presented data shows a synergistic effect of the combination of 6'SL and LNT on activation of the GPR35 receptor. This synergistic effect is maintained even when admixed with other human milk oligosaccharides. As outlined above, activation of the GPR35 receptor is linked to improved gut barrier.

Example 3

The following trials were done by digesting LNT and 6'SL and using the digested material to run the GPR35 activation assay, such as to validate the results of the trial of Example 2.

Digestion of LNT by β-Galactosidase

LNT was digested by β-galactosidase purified from aspergillus Niger (Megazyme, ref: E-AGLAN) using the following protocol: in a 1.5 ml screw cap tube with external thread, we mixed 84 mg of LNT in 900 µl of 100 mM acetate buffer (pH 4.5) and 100 µl of enzyme (400 U). This tube was incubated for 72 h at 55° C. in a ThermoMix shaker with 450 rpm shaking. The inactivation of the enzyme was done by heat treatment of 5 minutes at 100° C. The inactivated tube was stored at −20° C. until further analysis.

Digestion of 6'SL by Neuraminidase

6'SL was digested by neuraminidase purified from *Clostridium perfringens* (Megazyme, ref: E-SIALCP) using the following protocol: in a 1.5 ml screw cap tube with external thread, we mixed 78 mg of 6'SL in 900 µl of 50 mM phosphate buffer (pH 6.0) and 50 µl of enzyme (50 U). This tube was incubated for 72 h at 37° C. in a ThermoMix shaker with 450 rpm shaking. The inactivation of the enzyme was done by heat treatment of 5 minutes at 100° C. The inactivated tube was stored at −20° C. until further analysis.

Control of the Digestions

Figure 4A:
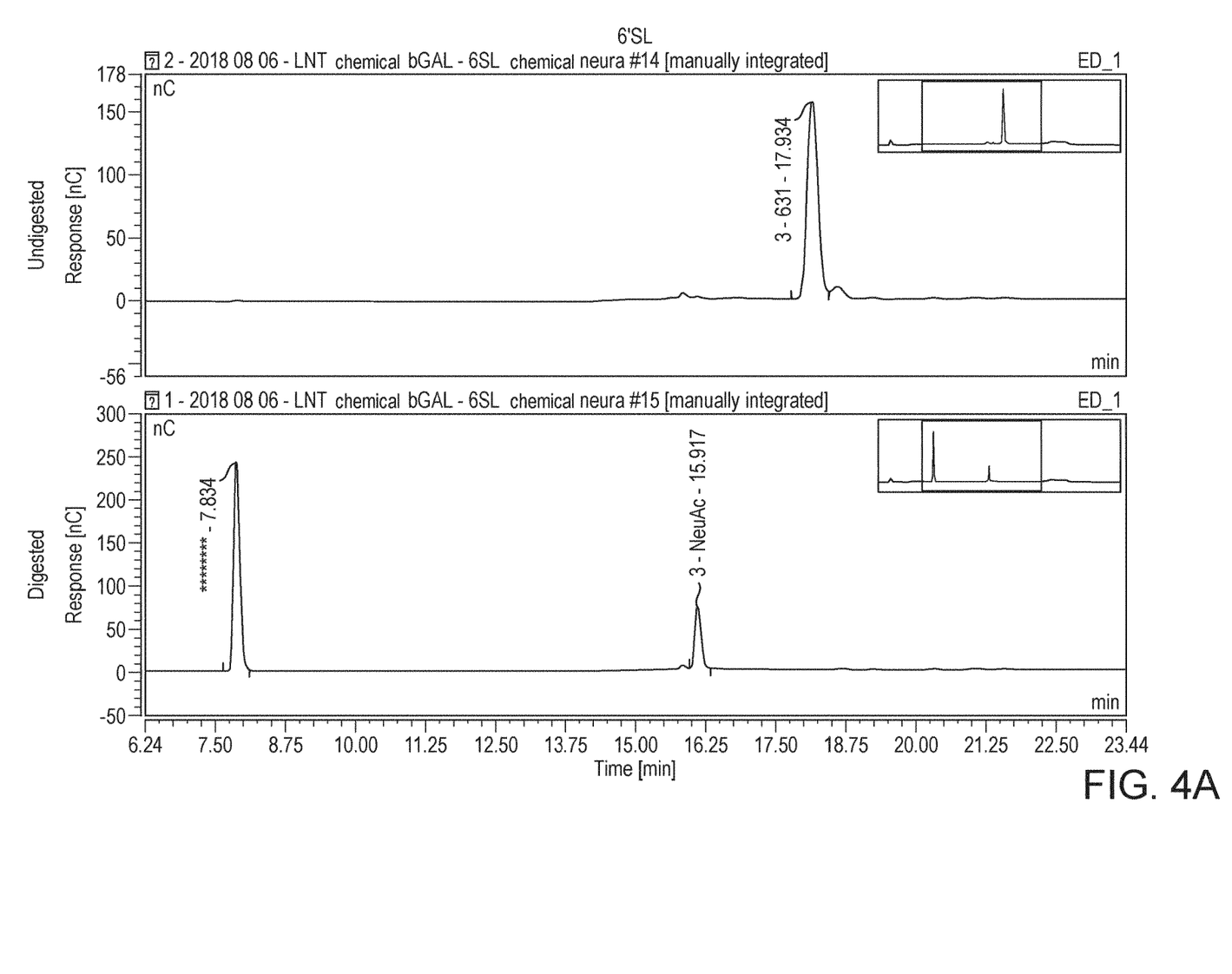
FIG. 4: HPAEC/PAD analysis of 6'SL (A) and LNT (B) before and after treatment with Neuraminidase (6'SL) or β-galactosidase (LNT) showing complete digestion of both HMOs
Figure 4B:
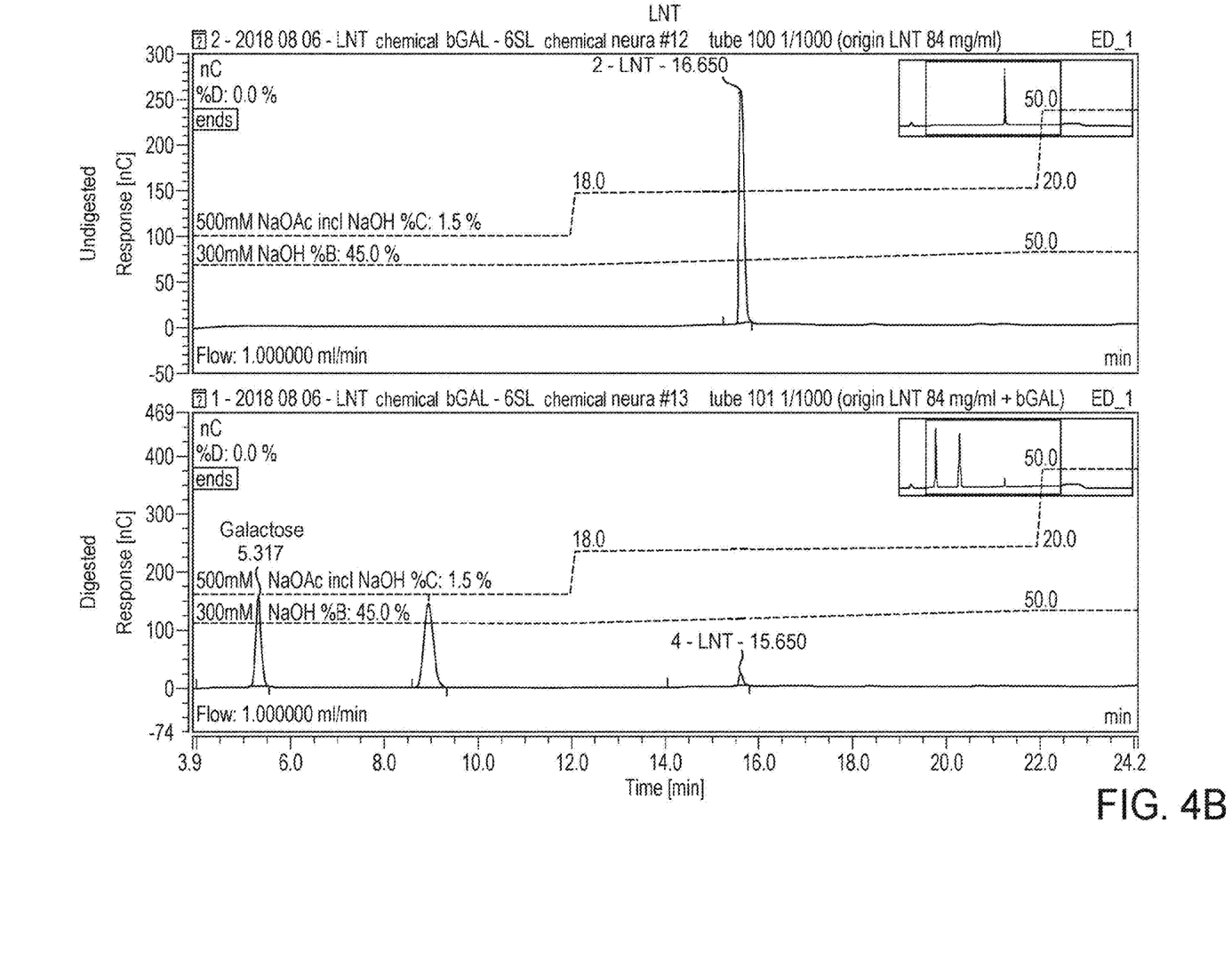

We confirmed that the digestions of LNT and 6'SL were complete by quantifying them using High Performance Anion Exchange Chromatography equipped with pulse amperometric detection (HPAEC-PAD). The results of the analysis are provided in FIG. 4. Peaks clearly confirm complete digestion of both LNT and 6'SL.

Preparation of Samples, Sample Tests and Results

Figure 5:
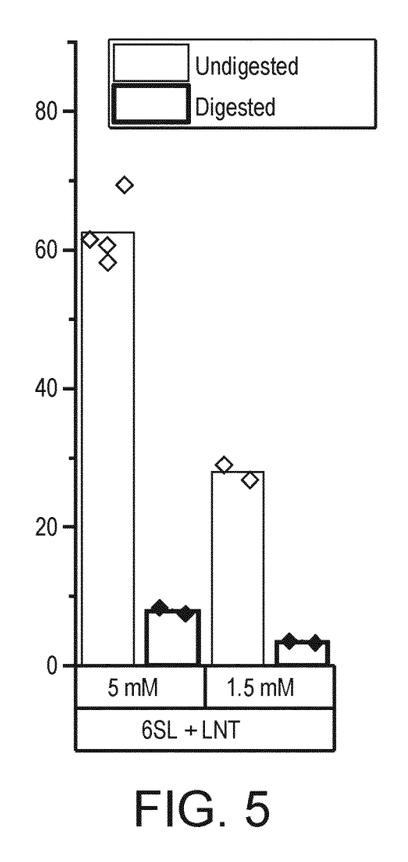
FIG. 5: In vitro response of GPR35 to HMO mix consisting of a mixture of 6'SL and LNT in the cell based assay of Example 2 (bars hashed with horizontal lines) compared with a mix of digested 6'SL and LNT (bars hashed with vertical lines). The graph shows that activity of the receptor is lost when 6'SL and LNT are digested.

The samples were diluted in 1×PBS (pH~7) at 5× concentrations and sent to DiscoverX. The GPR35 activation assay was performed as described in Example 2. The results are provided in FIG. 5. Response of GPR35 to digested and undigested mix of LNT and 6'SL showed a response with the undigested mix and background response to the digested mix, thereby demonstrating the specificity of the GPR35 response to LNT and 6'SL.

The invention claimed is:

1. A method of improving a gastrointestinal barrier in an infant, young child or child, the method comprising administering a nutritional composition comprising 6'-sialyllactose (6'SL) and lacto-N-tetraose (LNT) to the infant, young child or child,
   wherein the improving the gastrointestinal barrier comprises at least one of improving barrier structure and/or improving barrier protection,
   wherein the nutritional composition has at least one formulation that is: (i) the nutritional composition does not contain DFL and does not contain 3-FL, and/or (ii)

the nutritional composition does not contain LNnT, and/or (iii) the nutritional composition does not contain 3'-SL.

2. The method according to claim 1, wherein the improving the gastrointestinal barrier further comprises improving recovery of integrity of the gastrointestinal barrier.

3. The method according to claim 1, wherein the method is further for at least one of improving strength of the gastrointestinal barrier, improving the gastrointestinal barrier resistance, reducing disease susceptibility, reducing severity of symptoms upon inflammatory challenge of gastrointestinal mucosa and/or reducing the gastrointestinal barrier permeability.

4. The method according to claim 3, wherein the reducing the gastrointestinal barrier permeability comprises reducing at least one of pathogens, allergens and/or toxic compounds migrating from gut into body through intestinal barrier in the infant, young child or child.

5. The method according to claim 1, wherein the nutritional composition is formulated for administering to an infant.

6. The method according to claim 5, wherein the infant is selected from the group consisting of premature, small for gestational age and low birth weight babies.

7. The method according to claim 1, wherein the 6'SL and the LNT are present in a weight ratio of 6'SL:LNT from 3:1 to 1:3.

8. The method according to claim 1, wherein the 6'SL is present in an amount of 0.005 to 5 g/L of the nutritional composition on a dry weight basis.

9. The method according to claim 1, wherein the LNT is present in an amount of 0.005-3 g/L or 0.004-2.3 g/100g of nutritional composition on a dry weight basis.

10. The method according to claim 1, wherein
a) the 6'SL is present in an amount of 0.24 or 0.05 g/L of the nutritional composition or in an amount of 0.18 or 0.04 g/100g of the nutritional composition on a dry weight basis; and/or
b) the LNT is present in an amount of 0.5 g/L or 0.1 g/L of the nutritional composition or in an amount of 0.38 g/100g or 0.08 g/100g of the nutritional composition on a dry weight basis.

11. The method according to claim 1, wherein the nutritional composition is selected from the group consisting of an infant formula, a starter infant formula, a follow-on or follow-up infant formula, a growing-up milk, a baby food, an infant cereal composition, a fortifier and a supplement.

12. The method according to claim 6, wherein the infant was born premature.

* * * * *